United States Patent [19]
Schroeck

[11] Patent Number: 4,466,895
[45] Date of Patent: Aug. 21, 1984

[54] METAL SALTS OF LOWER DIALKYLPHOSPHORODITHIOIC ACIDS

[75] Inventor: Calvin W. Schroeck, Eastlake, Ohio

[73] Assignee: The Lubrizol Corporation, Wickliffe, Ohio

[21] Appl. No.: 508,369

[22] Filed: Jun. 27, 1983

[51] Int. Cl.³ .............................................. C10M 1/48
[52] U.S. Cl. .............................. 252/32.7 E; 252/46.7; 252/400 A; 260/429.9; 260/438.1; 260/439 R; 260/963
[58] Field of Search ................. 252/32.7 E, 46.7, 400; 260/429.9, 438.1, 439 R, 963

[56] References Cited
U.S. PATENT DOCUMENTS

| | | |
|---|---|---|
| 2,344,393 | 3/1944 | Cook et al. |
| 2,838,555 | 6/1958 | Goldsmith |
| 3,000,822 | 9/1981 | Higgins et al. |
| 3,190,833 | 6/1965 | Rhodes |
| 3,318,808 | 5/1967 | Plemich et al. |
| 3,413,327 | 11/1968 | Gordon |
| 3,843,530 | 10/1974 | Niedzielski ............. 252/32.7 E |
| 4,123,370 | 10/1978 | Meinhardt ............... 252/32.7 E |
| 4,306,984 | 12/1981 | Yamaguchi ............. 252/32.7 E |

Primary Examiner—Jacqueline V. Howard
Attorney, Agent, or Firm—Denis A. Polyn; Raymond F. Keller

[57] ABSTRACT

Certain metal salts of one or more dialkylphosphorodithioic acids are disclosed wherein
  (A) the alkyl groups each contain from two to four carbon atoms and at least one alkyl group is a butyl group,
  (B) the total number of carbon atoms per phosphorus atoms is less than 8,
  (C) from about 30 to 90 mole percent of the alkyl groups are primary alkyl groups,
  (D) from about 10 to 70 mole percent of the alkyl groups are secondary alkyl groups, and
  (E) the metal salt is a zinc, copper or iron salt, mixtures thereof, or a mixture of calcium salt and one or more of said metal salts; provided that when only 2 alkyl groups are present, from about 30 to 80 mole percent of the alkyl groups are n-butyl groups, from about 20 to 70 mole percent of the said alkyl groups are isopropyl groups.

These metal salts are oil-soluble and are useful as antioxidants and anti-wear agents particularly in lubricating oil compositions.

25 Claims, No Drawings

METAL SALTS OF LOWER DIALKYLPHOSPHORODITHIOIC ACIDS

BACKGROUND OF THE INVENTION

This invention relates to certain metal salts of lower alkyl phosphorodithioic acids, and, in particular, to such metal salts which are oil-soluble. Such metal salts are useful as antioxidants and antiwear agents particularly in lubricating oil compositions employed in the lubrication of internal combustion engines.

Metal salts of phosphorodithioic acids have been used widely as lubricant additives for inhibiting corrosion and improving extreme pressure properties. Obviously, for these purposes, oil-soluble materials are required. In addition to being oil-soluble to the extent required in a functional lubricating oil, it is preferred and desirable that the metal salts of phosphorodithioic acids be sufficiently oil-soluble to prepare oil concentrates of the salts. Oil concentrates may contain as much as 90% of the metal salts. One of the known techniques for improving the oil solubility of metal phosphorodithioates is to incorporate alkyl groups into the phosphorodithioic acid which contain a sufficient number of carbon atoms to provide oil solubility.

The procedures for preparing phosphorodithioic acids and their metal salts are well known in the art. The acids are prepared, for example, by the reaction of phosphorus pentasulfide with an alcohol or a phenol. The reaction involves 4 moles of the alcohol or phenol per mole of phosphorus pentasulfide and may be carried out within a temperature range of from about 50° C. to about 200° C. Hydrogen sulfide is liberated, and the residue is a defined acid. The preparation of the metal salt of phosphorodithioic acids may be effected by reaction of the acid with a metal neutralizing agent such as zinc, zinc oxide, barium oxide, etc. Simply mixing and heating these reactants is sufficient to cause the neutralization to take place, and the resulting product is sufficiently pure for use as a lubricant additive. Phosphorodithioic acids also have been prepared from mixtures of alcohols, and one advantage of the use of a mixture of alcohols is that the lower molecular weight, and expensive alcohols can be utilized in combination with the higher molecular weight, more expensive alcohols, and metal salts prepared from many such acids are oil-soluble.

Various suggestions have been made in the prior art regarding the nature, type, and carbon content of the alkyl or aryl groups present in dialkylphosphorodithioic acids used to prepare desired metal salts. For example, U.S. Pat. No. 2,344,393 taught that it was previously recognized that metal dithiophosphates should have one or more long chain alkyl groups to render them sufficiently soluble in lubricating oils to be of practical value. The patentees found, however that the zinc salt of diamylphosphorodithioic acid was oil-soluble. U.S. Pat. No. 3,318,808 discloses that the higher carbon containing alkyl groups (above 4 carbon atoms) enhance oil solubility. Thus, the patent teaches combinations of $C_4$ and lower primary and/or secondary alcohols with $C_5$ and above alcohols, and the ratio of the alcohols is selected to suit the balance between economics and solubility.

U.S. Pat. No. 3,190,833 describes oil-soluble metal phosphorodithioates which are the salts of metals in Group II of the periodic table and comprise preferably the salts of calcium, barium, strontium, zinc and cadmium with phosphorodithioic acids which contain a total of at least about 7.6 aliphatic carbon atoms per atom of phosphorus. To improve the oil solubility of the metal salts, they are reacted with up to about 0.75 mole of an epoxide.

Another patent which relates to the preparation of phosphorodithioic acid salts as useful additives in lubricants is U.S. Pat. No. 3,000,822. This patent describes zinc salts of a mixture of dialkylphosphorodithioic acids wherein the alkyl groups comprise a mixture of lower molecular weight primarily aliphatic hydrocarbon radicals having less than 5 carbon atoms and higher molecular weight primary aliphatic hydrocarbon radicals having at least 5 carbon atoms. The mole ratios of lower molecular weight radicals to higher molecular weight radicals in the zinc salt is within the range of 1:1 to 3:1.

Various suggestions have been made in the prior art for improving the utility of lower alkyl phosphorodithioic acid salts which have a tendency to be oil insoluble. U.S. Pat. No. 4,306,984 describes a procedure for rendering oil insoluble metal $C_2$–$C_3$ dialkyldithiophosphates oil-soluble by forming a complex between the dithiophosphate and an alkenyl or alkyl mono- or bis-succinimide. This combination of additives is used in lubricating oils which can be employed for crankcase lubrication of internal combustion engines. Another method which has been suggested for preparing noncrystalline mixtures of basic or mixed basic and neutral zinc salts of dialkyldithiophosphates containing from 1 to 13 carbon atoms in the alkyl groups has been suggested in U.S. Pat. No. 3,843,530. The mixtures of basic or mixed basic and neutral zinc salts described in this patent contain from 4 to 13 different alkyl groups, have an average carbon content of 3.5 to 4.5, and contain at least 12% by weight of zinc.

SUMMARY OF THE INVENTION

It now has been found that certain metal salts of lower dialkylphosphorodithioic acid containing 2 or more different alkyl groups containing from 2 to 4 carbon atoms can be prepared which are oil-soluble. The metal salt may be acid, neutral or basic metal salts.

More particularly, this invention relates to a metal salt of one or more dialkylphosphorodithioic acids wherein
(A) the alkyl groups each contain from two to four carbon atoms, and at least one alkyl group is a butyl group,
(B) the total number of carbon atoms per phosphorus atom is less than 8,
(C) from about 30 to 90 mole percent of the alkyl groups are primary alkyl groups,
(D) from about 10 to 70 mole percent of the alkyl groups are secondary alkyl groups, and
(E) the metal salt is a zinc, copper or iron salt, mixtures thereof, or a mixture of calcium salt and one or more of said metal salts; provided that when only 2 alkyl groups are present, from about 30 to 80 mole percent of the alkyl groups are n-butyl groups and, from about 20 to 70 mole percent of said alkyl groups are isopropyl groups.

The above metal salts are useful in lubricating oil compositions as antiwear agents and antioxidants.

DESCRIPTION OF THE PREFERRED EMBODIMENTS

The metal salts of dialkylpshosphorodithioic acids of this invention may be acidic salts, neutral salts, basic salts or mixtures thereof. The neutral or normal salts will contain about one equivalent of metal cation for each equivalent of acid; acid salts contain less than about one equivalent of metal cation for each equivalent of acid; and basic salts contain more than about one equivalent of metal cation for each equivalent of acid. Generally the salts will be the neutral or basic salts.

The total number of carbon atoms per phosphorus atom in the metal salts of the invention is less than 8. The alkyl groups which may be included in the salts of the invention include ethyl, n-propyl, isopropyl, n-butyl, isobutyl and secondary butyl, at least one of the alkyl groups being a butyl group. When three or more different alkyl groups are included, a small amount of methyl can be present. The alkyl groups present in the metal salts of the invention will comprise about 30 to 90 mole percent of primary alkyl groups and from about 10 to 70 mole percent of secondary alkyl groups. When only two alkyl groups are present in the metal salt, preferably from about 30 to 80 mole percent of the alkyl groups are n-butyl groups and from about 20 to 70 mole percent of the alkyl groups are isopropyl groups. In another preferred embodiment, from about 40 to 70 mole percent of the alkyl groups are primary alkyl groups and from about 30 to 60 mole percent are secondary alkyl groups.

As mentioned above, the metal salts of the dialkylphosphordithioic acids may contain more than two alkyl groups but generally, however, the salts of the invention will contain either two or three different alkyl groups. When the salts contain three or more different alkyl groups, from about 30 to 90 mole percent, and preferably from 30 to 80 mole percent of the alkyl groups are primary alkyl groups, and from about 10 to 70 mole percent, preferably 20 to 70 mole percent of the alkyl groups are secondary groups.

The metal salts of the invention may be zinc, copper or iron salts, mixtures thereof, or a mixture of a calcium salt and one or more of said metal salts. The zinc salts are the preferred metal salts.

The metal salts of this invention can be prepared by reaction of the phosphorodithioic acids with a metal neutralizing agent such as zinc, zinc oxide, copper oxide, iron oxide, etc. Generally, the salts will be prepared from a mixture of the phosphorodithioic acid, zinc oxide and water in a diluent such as mineral oil. Simply mixing and heating these reactants, is sufficient to cause a neutralization to take place and the resulting product, after stripping of water and excess alcohols, is sufficiently pure for the purposes of the invention. As mentioned earlier, neutral salts are prepared by reacting one equivalent of metal oxide or hydroxide with one equivalent of the phosphorodithioic acid. Basic metal salts are prepared by reacting an excess of (more than one equivalent) of the metal oxide or hydroxide with one equivalent of phosphorodithioic acid.

The phosphorodithioic acids utilized in the present invention are prepared by the reaction of phosphorus pentasulfide with a mixture of alcohols containing from 2 to 4 carbon atoms. The mixtures of alcohols utilized to prepare the dialkylphosphorodithioic acids utilized in the invention are mixtures which will contain from about 30 to 90 mole percent of primary alcohols and from about 10 to about 70 mole percent of secondary alcohols. The alcohols included in the alcohol mixture may be any one of the following: ethyl alcohol, n-propyl alcohol, isopropyl alcohol, n-butyl alcohol, isobutyl alcohol, and secondary butyl alcohol. Small amounts of methanol can be included in the alcohol mixtures. When oil-soluble metal salts of phosphorodithioic acids are desired, at least one of the alcohols should be a butyl alcohol. When an oil-soluble metal salt is desired, and only two alcohols are to be utilized in the mixture, the alcohol mixtures will comprise from about 30 to 80 mole percent of n-butyl alcohol and from 20 to 70 mole percent of an isopropyl alcohol.

Examples of suitable mixtures of 3 alcohols which are useful in preparing the phosphorodithioic acids used in the invention include: a mixture of n-butyl, isobutyl and isopropyl alcohols; a mixture of n-butyl, secondary butyl and ethyl alcohol; a mixture of isobutyl, secondary butyl and normal propyl alcohol; and a mixture of n-butyl, isopropyl and ethyl alcohol. The relative amounts of each alcohol in the mixture is not critical so long as the required limits of primary and secondary are maintained.

The preparation of the desired phosphorodithioic acids involves a reaction of 4 moles of the alcohol mixture per mole of phosphorus pentasulfide, and the reaction may be carried out within a temperature range of from about 50°–200° C. and preferably from about 80°–200° C., and preferably from about 80° C. to about 120° C. The reaction is completed in about 1 to 3 hours, and hydrogen sulfide is liberated during the reaction. The metal salts prepared in accordance with this invention are liquids which can be filtered at the end of the reaction.

The following examples illustrate the preparation of the phosphorodithioic acids and metal salts thereof. Unless otherwise indicated, all parts and percentages are by weight.

EXAMPLE 1A

A mixture of 259 parts (3.5 moles) of normal butyl alcohol and 90 parts (1.5 moles) of isopropyl alcohol is heated to 40° C. under a nitrogen atmosphere whereupon 244.2 parts (1.1 moles) of phosphorus pentasulfide are added in portions over a period of one hour while maintaining the temperature of the mixture of between about 55°–75° C. The mixture is maintained at this temperature for an additional 1.5 hours upon completion of the addition of the phosphorus pentasulfide and then cooled to room temperature. The reaction mixture is filtered through a filter aid, and the filtrate is the desired phosphorodithioic acid.

EXAMPLE 1B

Zinc oxide (67.7 parts, 1.65 equivalents) and 51 parts of mineral oil are charged to a one-liter flask and 410.1 parts (1.5 equivalents) of the phosphorodithioic acid prepared in Example 1A are added over a period of one hour while raising the temperature gradually to about 67° C. Upon completion of the addition of the acid, the reaction mixture is heated to 74° C. and maintained at this temperature for about 2.75 hours. The mixture is cooled to 50° C., and a vacuum is applied while raising the temperature to about 82° C. The residue is filtered, and the filtrate is the desired product. The product is a clear, yellow liquid containing 21.0% sulfur (19.81 theory), 10.71% zinc (10.05 theory), and 10.17% phosphorus (9.59 theory).

EXAMPLE 2A

A mixture of 240 (4 moles) parts of isopropyl alcohol and 444 parts of n-butyl alcohol (6 moles) is prepared under a nitrogen atmosphere and heated to 50° C. whereupon 504 parts of phosphorus pentasulfide (2.27 moles) are added over a period of 1.5 hours. The reaction is exothermic to about 68° C., and the mixture is maintained at this temperature for an additional hour after all of the phosphorus pentasulfide is added. The mixture is filtered through a filter aid, and the filtrate is the desired phosphorodithioic acid.

EXAMPLE 2B

A mixture of 162 parts (4 equivalents) of zinc oxide and 113 parts of a mineral oil is prepared, and 917 parts (3.3 equivalents) of the phosphorodithioic acid prepared in Example 2A are added over a period of 1.25 hours. The reaction is exothermic to 70° C. After completion of the addition of the acid, the mixture is heated for three hours at 80° C., and stripped to 100° C. at 35 mm. Hg. The mixture then is filtered twice through a filter aid, and the filtrate is the desired product. The product is a clear, yellow liquid containing 10.71% zinc (9.77 theory), 10.4% phosphorus and 21.35% sulfur.

EXAMPLE 3A

A mixture of 420 parts (7 moles) of isopropyl alcohol and 518 parts (7 moles) of n-butyl alcohol is prepared and heated to 60° C. under a nitrogen atmosphere. Phosphorus pentasulfide (647 parts, 2.91 moles) is added over a period of one hour while maintaining the temperature at 65°-77° C. The mixture is stirred an additional hour while cooling. The material is filtered through a filter aid, and the filtrate is the desired phosphorodithioic acid.

EXAMPLE 3B

A mixture of 113 parts (2.76 equivalents) of zinc oxide and 82 parts of mineral oil is prepared and 662 parts of the phosphorodithioic acid prepared in Example 3A are added over a period of 20 minutes. The reaction is exothermic and the temperature of the mixture reaches 70° C. The mixture then is heated to 90° C. and maintained at this temperature for three hours. The reaction mixture is stripped to 105° C. and 20 mm. Hg. The residue is filtered through filter aid, and the filtrate is the desired product containing 10.17% phosphorus, 21.0% sulfur and 10.98% zinc.

EXAMPLE 4A

A mixture of 360 parts (6 moles) of isopropyl alcohol and 296 parts (4 moles) of n-butyl alcohol is prepared and maintained in a nitrogen atmosphere while heating to 50° C. At this temperature, 504 parts (2.27 moles) of phosphorus pentasulfide are added over a period of 1.5 hours. The reaction is exothermic to 68° C., and the mixture is heated for an additional hour at 65° C. The mixture is filtered through a filter aid, and the filtrate is the desired phosphorodithioic acid.

EXAMPLE 4B

A mixture of 156 parts (3.8 equivalents) of zinc oxide and 110 parts of mineral oil is prepared, and 884 parts (3.3 equivalents) of the phosphorodithioic acid prepared in Example 4A are added in one hour. The reaction is exothermic to 80° C., and the mixture is maintained at 80° C. for an additional three hours. The mixture is stripped to 100° C. and 35 mm. Hg. and filtered. The filtrate is the desired product containing 11.27% zinc, 10.60% phosphorus and 21.65% sulfur.

EXAMPLE 5

A mixture of 69 parts (0.97 equivalent) of cuprous oxide and 38 parts of mineral oil is prepared and 239 parts (0.88 equivalent) of the phosphorodithioic acid prepared in Example 3A are added over a period of about two hours. The reaction is slightly exothermic during the addition, the mixture is thereafter stirred for an additional three hours while maintaining the temperature at about 70° C. The mixture is stripped to 105° C./10 mm. Hg. and filtered. The filtrate is a dark-green liquid containing 17.3% copper.

EXAMPLE 6

A mixture of 29.3 parts (1.1 equivalents) of ferric oxide and 33 parts of mineral oil was prepared, and 273 parts (1.0 equivalent) of the phosphorodithioic acid prepared in Example 3A are added over a period of two hours. The reaction is exothermic during the addition, and the mixture is thereafter stirred an additional 3.5 hours while maintaining the mixture at 70° C. The product is stripped to 105° C./10 mm. Hg. and filtered through filter aid. The filtrate is a black-green liquid containing 4.9% iron and 10.0% phosphorus.

EXAMPLE 7

A mixture of 239 parts (0.41 mole) of the product of Example 3B, 11 parts (0.15 mole) of calcium hydroxide and 10 parts of water is heated to about 80° C. and maintained at this temperature for six hours. The product is stripped to 105° C./10 mm. Hg. and filtered through filter aid. The filtrate is a molasses-colored liquid containing 2.19% calcium.

EXAMPLE 8A

A mixture of 74 parts (1 mole) of isobutyl alcohol, 111 parts (1.5 moles) of secondary butyl alcohol and 150 parts (2.5 moles) of normal propyl alcohol is prepared with stirring and heated to about 31° C. under a nitrogen atmosphere. Phosphorus pentasulfide (231 parts, 1.04 moles) is added to the alcohol mixture in about 0.7 hour while the temperature is maintained at between 58°-70° C. The mixture is stirred for approximately 1.5 additional hours allowing the temperature to drop to room temperature. After allowing the mixture to stand overnight, the mixture is filtered, and the filtrate is the desired phosphodithioic acid, a clear, gray-green liquid.

EXAMPLE 8B

A mixture of 79 parts (1.93 equivalents) of zinc oxide and 62 parts of mineral oil is prepared, and 514 parts (1.74 equivalents) of the phosphorodithioic acid of Example 8A are added in about 27 minutes. The reaction is exothermic to 68° C. and the mixture thereafter is heated to a temperature of about 80° C. The mixture is maintained at 80° C. for a period of three hours, stripped to 105° C./8 mm. Hg. and filtered. The filtrate is the desired product.

EXAMPLE 9A

A mixture of 185 parts (2.5 moles) of n-butyl alcohol, 74 parts (1.0 mole) of isobutyl alcohol and 90 parts (1.5 moles) of isopropyl alcohol is prepared with stirring under a nitrogen atmosphere. The mixture is heated to 60° C., and 231 parts (1.04 moles) of phosphorus pentasulfide are added over a period of about one hour while maintaining the temperature at about 58°–65° C. The mixture is stirred an additional 1.75 hours allowing the temperature to fall to room temperature. After standing overnight, the reaction mixture is filtered through paper, and the filtrate is the desired phosphorodithioic acid.

EXAMPLE 9B

A mixture of 64 parts of mineral oil and 84 parts (2.05 equivalents) of zinc oxide is prepared with stirring, and 525 parts (1.85 equivalents) of the phosphorodithioic acid prepared in Example 9A are added over a period of 0.5 hour with an exotherm to 65° C. The mixture is heated to 80° C. and maintained at that temperature for three hours. The mixture is stripped to 106° C./8 mm. Hg. The residue is filtered through filter aid, and the filtrate is the desired product, a clear amber liquid.

EXAMPLE 10A

The mixture of 111 parts (1.5 moles) of n-butyl alcohol, 148 parts (2.0 moles) of secondary butyl alcohol and 90 parts (1.5 moles) of isopropyl alcohol is prepared in a nitrogen atmosphere and heated to about 63° C. Phosphorus pentasulfide (231 parts, 1.04 moles) is added in about 1.3 hours with an exotherm to about 55°–65° C. The mixture is stirred an additional 1.75 hours allowing the temperature to fall to room temperature. After allowing the mixture to stand overnight, the mixture is filtered through paper, and the filtrate is the desired phosphorodithioic acid, a clear, green-gray liquid.

EXAMPLE 10B

A mixture of 80 parts (1.95 equivalents) of zinc oxide and 62 parts (1.77 equivalents) of mineral oil is prepared and 520 parts of the phosphorodithioic acid prepared in Example 10A are added over a period of 25 minutes with an exotherm to 66° C. The mixture is heated to a temperature of 80° C. and maintained between 80°–88° C. for five hours. The mixture then is stripped to 105° C./9 mm. Hg. The residue is filtered through a filter aid, and the filtrate is the desired product, a clear, greenish-gold liquid.

EXAMPLE 11A

A mixture of 166.5 parts (2.25 moles) of n-butyl alcohol, 277.5 parts (3.75 moles) of secondary butyl alcohol and 69 parts (1.50 moles) of ethanol is prepared in a nitrogen atmosphere and heated to 50° C. Phosphorus pentasulfide (377.5 parts, 1.70 moles) is added in small portions while the temperature rises to about 75°–80° C. The temperature is maintained at about 70°–75° C. for about two hours. After cooling the mixture to room temperature, it is filtered through filter aid, and the filtrate is the desired phosphorodithioic acid.

EXAMPLE 11B

A mixture of 67.7 parts (1.65 equivalents) of zinc oxide and 50.3 parts of mineral oil is prepared, and 405 parts (1.5 equivalents) of the phosphorodithioic acid prepared in Example 11A are added dropwise over a period of one hour. The reaction is exothermic and the temperature of the mixture reaches 65° C. Following the addition, the mixture is heated to 75° C. and maintained at a temperature between 75°–78° C. for three hours. The temperature of the mixture is reduced to 50° C., and the mixture is stripped to 95° C./15 mm. Hg. The residue is filtered two times through a filter aid, and the filtrate is the desired product, a yellow-green liquid containing 10.84% zinc.

EXAMPLE 12A

A mixture of 296 parts (4 moles) of n-butyl alcohol, 240 parts (4 moles) of isopropyl alcohol and 92 parts (2 moles) of ethanol is warmed to 40° C. under a nitrogen atmosphere, and phosphorus pentasulfide (504 parts, 2.7 moles) is added slowly over a period of about 1.5 hours while maintaining the reaction temperature at about 65°–70° C. Following completion of the addition of the phosphorus pentasulfide, the reaction mixture is maintained at this temperature for an additional 1.5 hours. After cooling to 40° C., the mixture is filtered through filter aid. The filtrate is the desired phosphorodithioic acid.

EXAMPLE 12B

A mixture of 112.7 parts (2.7 equivalents) of zinc oxide and 79.1 parts of mineral oil is prepared, and 632.3 parts (2.5 equivalents) of the phosphorodithioic acid prepared in Example 12A are added over a period of two hours while maintaining the reaction temperature at about 65° C. or less. The mixture then is heated to 75° C. and maintained at this temperature for three hours. The mixture then is stripped to 100° C./15 mm. Hg., and the residue is filtered through filter aid. The filtrate is the desired product, and is a clear, yellow liquid containing 11.04% zinc.

EXAMPLE 13A

A mixture of 296 parts (4 moles) of n-butyl alcohol, 148 parts (2 moles) of secondary butyl alcohol, and 240 parts (4 moles) of isopropyl alcohol is prepared under a nitrogen atmosphere and heated to 62° C. Phosphorus pentasulfide (463 parts, 2.08 moles) is added to the mixture over a period of about 52 minutes (at which time the temperature of the reaction mixture ranges from 59°–70° C.). The mixture is stirred for an additional hour whereupon the temperature falls to about 45° C. The reaction mixture is filtered through filter aid and the filtrate is the desired phosphorodithioic acid.

EXAMPLE 13B

A mixture of 79 parts (1.93 equivalents) of zinc oxide and 62 parts of mineral oil is prepared, and 501 parts (1.75 equivalents) of the phosphorodithioic acid prepared in Example 12A are added in about 0.5 hour with the reaction temperature reaching 66° C. Thereafter, the reaction mixture is heated to about 80° C. and maintained at this temperature for about three hours. The mixture then is stripped to 104° C./17 mm. Hg. and filtered. The filtrate is the desired product which is a clear, yellow-green liquid.

EXAMPLE 14

A phosphorodithioic acid is prepared in accordance with the general procedure of Example 3A utilizing n-butyl alcohol, secondary butyl alcohol and isopropyl alcohol and the molar ratio of 3:2:5. A mixture of 60 parts of mineral oil and 90 parts (2.2 equivalents) of zinc oxide is prepared and 494 parts of the phosphorodithioic acid is added over a period of about 24 minutes. The reaction is exothermic and the temperature of the mixture reaches about 69° C. The mixture then is heated to about 80° C. and maintained at this temperature for three hours. The mixture is stripped to 104° C. and 10 mm. hg. The residue is filtered through a filter aid, and the filter aid is the desired product which is a clear yellow liquid. This zinc salt product is soluble in mineral oil concentrations of up to 10% and more.

As previously indicated, the metal salt compositions of this invention are oil soluble and are useful as additives for lubricants in which they can function primarily as oxidation inhibitors, antiwear agents and/or extreme pressure agents. Oil-soluble for the purposes of this application means that the metal salts are soluble in mineral oil such as a 100 neutral oil at a concentration of up to at least about 1% and preferably up to at least about 10% or more. They can be employed in a variety of lubricants based on diverse oils of lubricating viscosity, including natural and synthetic lubricating oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. They can also be used in gas engines, stationary power engines and turbines and the like. Automatic transmission fluids, transaxle lubricants, gear lubricants, metal-working lubricants, hydraulic fluids and other lubricating oil and grease compositions can also benefit from the incorporation therein of the compositions of the present invention Natural oils include animal oils and vegetable oils (e.g., castor, lard oil) liquid petroleum oils and solvent-treated or acid-treated mineral lubricating oils of the paraffinic, naphthenic and mixed paraffinic-naphthenic types. Oils of lubricating viscosity derived from coal or shale are also useful base oils.

Synthetic lubricating oils include hydrocarbon oils and halo-substituted hyrocarbon oils such as polymerized and interpolymerized olefins [e.g., polybutylenes, polypropylenes, propylene-isobutylene copolymers, chlorinated polybutylenes, poly(1-hexenes), poly(1-octenes), poly(1-decenes)]; alkylbenzenes (e.g., dodecylbenzenes, tetradecylbenzenes, dinonylbenzenes, di(2-ethylhexyl)benzenes]; polyphenyls (e.g. biphenyls, terphenyls, alkylated polyphenols); and alkylated diphenyl ethers and alkylated diphenyl sulfides and the derivatives, analogs and homologs thereof.

Alkylene oxide polymers and interpolymers and derivatives thereof where the terminal hydroxyl groups have been modified by esterification, etherification, etc., constitute another class of known synthetic lubricating oils. These are exemplified by polyoxyalkylene polymers prepared by polymerization of ethylene oxide or propylene oxide, the alkyl and aryl ethers of these polyoxyalkylene polymers (e.g., methyl-polyisopropylene glycol ether having an average molecular weight of 1000, diphenyl ether of poly-ethylene glycol having a molecular weight of 500–1000, diethyl ether of polypropylene glycol having a molecular weight of 1000–1500); and mono- and polycarboxylic esters thereof, for example, the acetic acid esters, mixed $C_3$–$C_8$ fatty acid esters and $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkylmalonic acids, alkenyl malonic acids) with a variety of alcohols (e.g., butyl alcohol, hexyl alcohol, dodecyl alcohol, 2-ethylhexyl alcohol, ethylene glycol, diethylene glycol monoether, propylene glycol). Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol and tripentaerythritol.

Silicon-based oils such as the polyalkyl-, polyaryl-, polyalkoxy-, or polyaryloxysiloxane oils and silicate oils comprise another useful class of synthetic lubricants; they include tetraethyl silicate, tetraisopropyl silicate, tetra-(2-ethylhexyl)silicate, tetra-(4-methyl-2-ethylhexyl)silicate, tetra-(p-tertbutylphenyl)silicate, hexa-(4-methyl-2-pentoxy)disiloxane, poly(methyl)siloxanes and poly(methylphenyl)siloxanes. Other synthetic lubricating oils include liquid esters of phosphorus-containing acids (e.g. tricresyl phosphate, trioctyl phosphate, diethyl ester of decylphosphonic acid) and polymeric tetrahydrofurans.

Unrefined, refined and rerefined oils can be used in the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques, such as distillation, solvent extraction, acid or base extraction, filtration and percolation are known to those skilled in the art. Rerefined oils are obtaned by processes similar to those used to obtain refined oils applied to refined oils which have been already used in service. Such rerefined oils are also known as reclaimed or reprocessed oils and often are additionally processed by techniques for removal of spent additives and oil breakdown products.

Generally the lubricants of the present invention contain a lubricating improving amount of one or more of the metal salts of this invention, e.g., sufficient to provide it with improved oxidation stability, and/or antiwear and/or extreme pressure properties. These salts have additional properties such as corrosion inhibition. Normally the amount employed will be about 0.05% to about 20%, preferably about 0.1% to about 10% of the total weight of the lubricating composition. This amount is exclusive of solvent/diluent medium. In lubricating compositions operated under extremely adverse conditions, such as lubricating compositions for marine diesel engines, the metal salts of this invention may be present in amounts of up to about 30% by weight, or more, of the total weight of the lubricating composition.

The invention also contemplates the use of other additives in combination with the metal salt compositions of this invention. Such additives include, for example, detergents, dispersants of the ash-producing or ashless type, corrosion- and oxidation-inhibiting agents, pour point depressing agents, extreme pressure agent, antiwear agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature about 50° C. and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-$\beta$-naphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°-200° C.

Ashless detergents and dispersants are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art, and any of them are suitable for use in the coolant fluid compositions of this invention. The following are illustrative:

(1) Reaction products of carboxylic acids (or derivatives thereof) containing at least about 34 and preferably at least about 54 carbon atoms with nitrogen containing compounds such as amine, organic hydroxy compounds such as phenols and alcohols, and/or basic inorganic materials. Examples of these "carboxylic dispersants" are described in British Pat. No. 1,306,529 and in many U.S. patents including the following:

| | | |
|---|---|---|
| 3,163,603 | 3,351,552 | 3,541,012 |
| 3,184,474 | 3,381,022 | 3,543,678 |
| 3,215,707 | 3,399,141 | 3,542,680 |
| 3,219,666 | 3,415,750 | 3,567,637 |
| 3,271,310 | 3,433,744 | 3,574,101 |
| 3,272,746 | 3,444,170 | 3,576,743 |
| 3,281,357 | 3,448,048 | 3,630,904 |
| 3,306,908 | 3,448,049 | 3,632,510 |
| 3,311,558 | 3,451,933 | 3,632,511 |
| 3,316,177 | 3,454,607 | 3,697,428 |
| 3,340,281 | 3,467,668 | 3,725,441 |
| 3,341,542 | 3,501,405 | 4,234,435 |
| 3,346,493 | 3,522,179 | Re 26,433 |

(2) Reaction products of relatively high molecular weight aliphatic or alicyclic halides with amines, preferably polyalkylene polyamines. These may be characterized as "amine dispersants" and examples thereof are described for example, in the following U.S. patents:

| | |
|---|---|
| 3,275,554 | 3,454,555 |
| 3,438,757 | 3,565,804 |

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. patents are illustrative:

| | | |
|---|---|---|
| 2,459,112 | 3,442,808 | 3,591,598 |
| 2,962,442 | 3,448,047 | 3,600,372 |
| 2,984,550 | 3,454,497 | 3,634,515 |
| 3,036,003 | 3,459,661 | 3,649,229 |
| 3,166,516 | 3,461,172 | 3,697,574 |
| 3,236,770 | 3,493,520 | 3,725,277 |
| 3,355,270 | 3,539,633 | 3,725,480 |
| 3,368,972 | 3,558,743 | 3,726,882 |
| 3,413,347 | 3,586,629 | 3,980,569 |

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. patents:

| | | | |
|---|---|---|---|
| 3,036,003 | 3,282,955 | 3,493,520 | 3,639,242 |
| 3,087,936 | 3,312,619 | 3,502,677 | 3,649,229 |
| 3,200,107 | 3,366,569 | 3,513,093 | 3,649,659 |
| 3,216,936 | 3,367,943 | 3,533,945 | 3,658,836 |
| 3,254,025 | 3,373,111 | 3,539,633 | 3,697,574 |
| 3,256,185 | 3,403,102 | 3,573,010 | 3,702,757 |
| 3,278,550 | 3,442,808 | 3,579,450 | 3,703,536 |
| 3,280,234 | 3,455,831 | 3,591,598 | 3,704,308 |
| 3,281,428 | 3,455,832 | 3,600,372 | 3,708,422 |

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-subsituted acrylates. These may be characterized as "polymeric dispersants" and examples thereof are disclosed in the following U.S. patents:

| | |
|---|---|
| 3,329,658 | 3,666,730 |
| 3,449,250 | 3,687,849 |
| 3,519,565 | 3,702,300 |

The above-noted patents are incorporated by reference herein for their disclosures of ashless dispersants.

Extreme pressure agents and corrosion- and oxidation-inhibiting agents are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate, phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

Pour point depressants are a particularly useful type of additive often included in the lubricating oils described herein. The use of such pour point depressants in oil-based compositions to improve low temperature properties of oil-based compositions is well known in the art. See, for example, page 8 of "Lubricant Additives" by C. V. Smalheer and R. Kennedy Smith (Lezius-Hiles Co. publishers, Cleveland, Ohio, 1967).

Examples of useful pour point depressants are polymethacrylates, polyacrylates; polyacrylamides; condensation products of haloparaffin waxes and aromatic compounds; vinyl carboxylate polymers; and terpolymers of dialkylfumarates, vinylesters of fatty acids and alkylvinylethers. Pour point depressants useful for the purposes of this invention, techniques for their preparation and their uses are described in U.S. Pat. Nos. 2,387,501; 2,015,748; 2,655,479; 1,815,022; 2,191,498; 2,666,746; 2,721,877; 2,721,878; and 3,250,715 which are hereby incorporated by reference for their relevant disclosures.

The metal salt compositions of this invention can be added directly to the lubricant. Preferably, however, they are diluted with a substantially inert, normally liquid organic diluent such as mineral oil, naphtha, benzene, toluene or xylene, to form an additive concentrate. These concentrates usually contain from about 5% to 90% by weight of the metal salts of this invention and may contain, in addition, one or more other additives known in the art or described hereinabove. The remainder of the concentrate is the substantially inert normally liquid diluent.

Illustrative concentrates and lubricants of this invention are listed in Table I. All amounts are by weight.

TABLE I

| Concentrate A | |
|---|---|
| Product of Example 1B | 20 |
| Mineral Oil | 80 |
| Concentrate B | |
| Product of Example 3B | 15 |
| Mineral Oil | 85 |
| Concentrate C | |
| Product of Example 3B | 20 |
| Reaction product of polybutenyl succinic anhydride with ethylene polyamine and pentaerythritol | 10 |
| Mineral Oil | 70 |
| Lubricant D | |
| Product of Example 1B | 2.00 |
| Mineral Oil | 98.00 |
| Lubricant E | |
| Product of Example 3B | 2.00 |
| Reaction product of polybutenyl succinic anhydride with ethylene polyamine and pentaerythritol | 1.80 |
| Basic calcium sulfurized tetrapropenylphenate | 2.50 |
| Mineral Oil | 95.70 |

Additional lubricating compositions are shown in Table II

TABLE II

| Components | Lubricant Examples | | | | |
|---|---|---|---|---|---|
| | F | G | H | I | J |
| Base oil | 85.81 | 80.25 | 93.82 | 85.07 | 78.63 |
| Product of Example 3B | .49 | .36 | .53 | .54 | .54 |
| Polybutenyl succinic anhydride-ethylene polyamine reaction product | 3.65 | 3.10 | 3.09 | 3.65 | 3.65 |
| Reaction product of polybutenyl succinic anhydride with ethylene polyamine and pentaerythritol | | 2.94 | | | |
| Reaction product of maleic anhydride-styrene copolymer with alcohol and amine | .31 | | | .21 | .21 |
| Hydrogenated styrene isoprene non-dispersant viscosity improver | 7.46 | | | 7.94 | 14.38 |
| Ethylene-propylene polymeric viscosity improver | | 7.81 | | | |
| Methacrylate copolymer | | | .05 | | |
| Zinc dialkylphosphorodithioate | .63 | 1.31 | .58 | .59 | .59 |
| Sulfurized Diels Alder adduct | .20 | | .33 | .33 | .33 |
| Alkylated aryl amine | .11 | | .17 | .17 | .17 |
| Basic calcium petroleum sulfonate | .54 | 1.19 | 1.00 | 1.01 | 1.01 |
| Basic magnesium petroleum sulfonate | .42 | .45 | .43 | .44 | .44 |
| Basic sodium petroleum sulfonate | .36 | | | | |
| Sulfurized tetrapropenylphenol | | 2.47 | | | |
| Alkenyl succinic anhydride-alcohol reation product | | | | .05 | .05 |
| Nonylphenoxypoly (ethyleneoxy) ethanol | | .12 | | | |
| Silicone antifoam agent | .005 | .01 | .006 | .007 | .007 |

What is claimed is:

1. A metal salt of one or more dialkylphosphorodithioic acids wherein
   (A) the alkyl groups each contain from two to four carbon atoms and at least one alkyl group is a butyl group,
   (B) the total number of carbon atoms per phosphorus atom is less than 8, (C) from about 30 to 90 mole percent of the alkyl groups are primary alkyl groups, (D) from about 10 to 70 mole percent of the alkyl groups are secondary alkyl groups, and (E) the metal salt is a zinc, copper or iron salt, mixtures thereof, or a mixture of calcium salt and one or more of said metal salts; provided that when only 2 alkyl groups are present, from about 30 to 80 mole percent of the alkyl groups are n-butyl groups, from about 20 to 70 mole percent of the said alkyl groups are isopropyl groups.

2. The metal salt of claim 1 wherein from about 40 to 70 mole percent of the alkyl groups are primary alkyl groups and from about 30 to 60 mole percent of the alkyl groups are secondary alkyl groups.

3. The metal salt of claim 1 wherein there are present at least three different alkyl groups.

4. The metal salt of claim 1 wherein there are three different alkyl groups.

5. The metal salt of claim 4 wherein the metal is zinc.

6. The metal salt of claim 1 wherein the salt is a neutral salt, basic salt, or a mixture thereof.

7. A metal salt of one or more dialkylphosphorodithioic acids wherein (A) from about 30 to 80 mole percent of the alkyl groups are n-butyl groups, (B) from about 20 to 70 mole percent of the alkyl groups are isopropyl groups, and (C) the metal salt is a zinc, copper, or iron salt, mixtures thereof, or a mixture of calcium salt and one or more of said metal salt.

8. The metal salt of claim 7 wherein from about 40 to 70 mole percent of the alkyl groups are n-butyl groups and from about 30 to 60 mole percent of the alkyl groups are isopropyl groups.

9. The metal salt of claim 7 wherein the metal is zinc.

10. The metal salt of claim 7 wherein the alkyl groups are a mixture of about 50 mole percent of n-butyl groups and 50 mole percent of isopropyl groups.

11. The metal salt of claim 7 wherein the salt is a neutral salt, basic salt, or a mixture thereof.

12. A metal salt of one or more dialkylphosphorodithioic acids containing more than two different alkyl groups wherein (A) the alkyl groups each contain from two to four carbon atoms and at least one alkyl group is a butyl group, (B) the total number of carbon atoms per phosphorus atom is less than 8, (C) from about 30 to 90 mole percent of the alkyl groups are primary alkyl groups, (D) from about 10 to 70 mole percent of the alkyl groups are secondary groups and (E) the metal salt is a zinc, copper or iron salt, mixtures thereof, or a mixture of calcium salt and one or more of said metal salt.

13. The metal salt of claim 12 wherein about 30 to 80 mole percent of the alkyl groups are primary alkyl groups and from about 20 to 70 mole percent of the alkyl groups are secondary groups.

14. The metal salt of claim 13 wherein there are three different alkyl groups.

15. The metal salt of claim 14 wherein the alkyl groups comprise a mixture of isobutyl, secondary butyl and normal propyl groups.

16. The metal salt of claim 14 wherein the alkyl groups comprise a mixture of n-butyl, isobutyl and isopropyl groups.

17. The metal salt of claim 14 wherein the alkyl groups comprise a mixture of n-butyl, secondary butyl and ethyl groups.

18. The metal salt of claim 14 wherein the alkyl groups comprise a mixture of n-butyl, isopropyl and ethyl groups.

19. The metal salt of claim 12 wherein the salt is a neutral salt, basic salt, or a mixture thereof.

20. An additive concentrate comprising a substantially inert, normally liquid organic diluent and from about 5 to about 90 percent of the metal salt of claim 1.

21. An additive concentrate comprising a substantially inert, normally liquid organic diluent and from about 5 to about 90 percent by weight of the composition of claim 7.

22. An additive concentrate comprising a substantially inert, normally liquid organic diluent and from about 5 to about 90 percent by weight of the metal salt of claim 12.

23. A lubricant composition comprising a major amount of a lubricating oil and a minor amount of the metal salt of claim 1.

24. A lubricant composition comprising a major amount of a lubricating oil and a minor amount of the metal salt of claim 7.

25. A lubricant composition comprising a major amount of a lubricating oil and a minor amount of the metal salt of claim 12.

* * * * *